(12) United States Patent
Kubo et al.

(10) Patent No.: US 11,122,015 B2
(45) Date of Patent: Sep. 14, 2021

(54) DATA TRANSMITTING APPARATUS

(71) Applicants: OMRON HEALTHCARE CO., LTD., Muko (JP); OMRON Corporation, Kyoto (JP)

(72) Inventors: Nobuo Kubo, Kyoto (JP); Toru Deno, Kyoto (JP); Hideki Kondo, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 89 days.

(21) Appl. No.: 16/701,317

(22) Filed: Dec. 3, 2019

(65) Prior Publication Data

US 2020/0106753 A1 Apr. 2, 2020

Related U.S. Application Data

(63) Continuation of application No. PCT/JP2018/028815, filed on Aug. 1, 2018.

(30) Foreign Application Priority Data

Aug. 9, 2017 (JP) .............................. JP2017-154755

(51) Int. Cl.
| | | |
|---|---|---|
| *H04L 29/06* | (2006.01) | |
| *A61B 5/022* | (2006.01) | |
| *G01N 33/487* | (2006.01) | |
| *H04L 12/54* | (2013.01) | |
| *H04W 12/00* | (2021.01) | |
| *H04W 12/033* | (2021.01) | |
| *H04W 4/80* | (2018.01) | |

(52) U.S. Cl.
CPC ...... *H04L 63/0428* (2013.01); *A61B 5/02225* (2013.01); *G01N 33/48792* (2013.01); *H04L 12/56* (2013.01); *H04W 12/033* (2021.01); *A61M 2205/3584* (2013.01); *H04W 4/80* (2018.02)

(58) Field of Classification Search
None
See application file for complete search history.

(56) References Cited

U.S. PATENT DOCUMENTS

| | | | |
|---|---|---|---|
| 10,226,188 B2 * | 3/2019 | Watson | ................ A61B 5/7221 |
| 2002/0115912 A1 | 8/2002 | Muraki et al. | |

(Continued)

FOREIGN PATENT DOCUMENTS

| | | |
|---|---|---|
| CN | 101263675 A | 9/2008 |
| CN | 101888514 A | 11/2010 |

(Continued)

OTHER PUBLICATIONS

Official Communication issued in International Patent Application No. PCT/JP2018/028815, dated Sep. 18, 2018.

(Continued)

*Primary Examiner* — Tri H Phan
(74) *Attorney, Agent, or Firm* — Keating & Bennett LLP

(57) ABSTRACT

According to an aspect of the invention, a data transmitting apparatus includes a transmitting unit that transmits a first packet through a unidirectional communication based on an instruction to transmit the first packet, and that transmits a second packet through a unidirectional communication based on an instruction to transmit the second packet.

5 Claims, 6 Drawing Sheets

(56) References Cited

U.S. PATENT DOCUMENTS

| | | | |
|---|---|---|---|
| 2007/0061409 A1 | 3/2007 | Rydenhag | |
| 2008/0058614 A1 | 3/2008 | Banet et al. | |
| 2010/0293287 A1 | 11/2010 | Kobayashi | |
| 2010/0298662 A1 | 11/2010 | Yu et al. | |
| 2012/0033807 A1 | 2/2012 | Asim et al. | |
| 2012/0143621 A1 | 6/2012 | Lee et al. | |
| 2015/0201289 A1 | 7/2015 | Solum et al. | |
| 2015/0264147 A1 | 9/2015 | Lin et al. | |
| 2016/0029149 A1 | 1/2016 | Morikawa et al. | |
| 2016/0081597 A1* | 3/2016 | Bhavaraju | A61B 5/7221 600/365 |
| 2016/0106350 A1* | 4/2016 | Bhavaraju | A61M 5/1723 600/365 |
| 2016/0295618 A1 | 10/2016 | Kimura et al. | |
| 2017/0187828 A1 | 6/2017 | Soji et al. | |
| 2017/0357825 A1* | 12/2017 | Takahashi | G06F 21/6245 |
| 2020/0106571 A1* | 4/2020 | Kubo | A61B 5/0022 |

FOREIGN PATENT DOCUMENTS

| | | |
|---|---|---|
| CN | 102388386 A | 3/2012 |
| CN | 102682193 A | 9/2012 |
| CN | 105141328 A | 12/2015 |
| CN | 105518692 A | 4/2016 |
| CN | 105743752 A | 7/2016 |
| CN | 105933378 A | 9/2016 |
| CN | 106333667 A | 1/2017 |
| JP | 55-119704 U | 8/1980 |
| JP | 2000-083907 A | 3/2000 |
| JP | 2007-130210 A | 5/2007 |
| JP | 2009-240530 A | 10/2009 |
| JP | 2012-527308 A | 11/2012 |
| JP | 2015-70284 A | 4/2015 |
| JP | 5852620 B2 | 2/2016 |
| JP | 2016-131313 A | 7/2016 |
| JP | 2016-195325 A | 11/2016 |
| JP | 2017-118405 A | 6/2017 |

OTHER PUBLICATIONS

Official Communication issued in corresponding Chinese Patent Application No. 201880041473.2, dated Oct. 12, 2020.
English translation of Official Communication issued in International Patent Application No. PCT/JP2018/028815, dated Feb. 13, 2020.
Official Communication issued in corresponding Japanese Patent Application No. 2017-154755, dated May 18, 2021.
Official Communication issued in corresponding Chinese Patent Application No. 201880041473.2, dated Jul. 2, 2021.

* cited by examiner

DATA TRANSMITTING APPARATUS

This application is a Continuation Application of PCT Application No. PCT/JP2018/028815, filed Aug. 1, 2018 and based upon and claiming the benefit of priority from Japanese Patent Application No. 2017-154755, filed Aug. 9, 2017, the entire contents of all of which are incorporated herein by reference.

FIELD

The present invention relates to a data transmitting apparatus.

BACKGROUND

Blood pressure monitors equipped with a function of transferring blood pressure data to a user's portable information terminal have been launched onto the market. As the portable information terminal, a smartphone, a tablet terminal, or a notebook personal computer, for example, is used. By employing such a function, the user can view, on the portable information terminal, the results of the measurements of the user's blood pressures in various situations. For the transfer of blood pressure data, short-range wireless communication technology is typically used, Bluetooth (registered trademark) in particular. In general, Bluetooth-based communications (connections) can be implemented on a small scale and in a manner which saves power, compared to wireless local area network (WLAN) communications. The Bluetooth specification Version 4.0, also called Bluetooth Low Energy (BLE), is capable of further reducing the power consumption, as compared to the legacy specifications.

BLE allows for bidirectional communications called "connections". However, connections come with certain problems, such as the complexity of operations required of users for pairing; the complexity of communication procedures following the pairing; the necessity for the portable information terminal side to support BLE; the necessity for the blood pressure monitor, as well as the portable information terminal, to install high-performance hardware (processor, memory, etc.); high development and appraisal costs; and unsuitability for low-capacity data transmissions due to the heaviness of the communication overhead.

On the other hand, BLE also allows for unidirectional communications called "advertising". Japanese Patent No. 5852620 discloses a technique for transmitting an advertisement packet by including given data in a margin area of its data field.

SUMMARY

If the blood pressure monitor transmits blood pressure data through the employment of advertising, a portable information terminal capable of receiving advertisements can receive blood pressure data without the need for pairing or subsequent complicated communication procedures.

However, since the blood pressure data transmitted from the blood pressure monitor can be received by any portable information terminal capable of receiving advertisements, the risk of a decrease in the degree of confidentiality of the blood pressure data exists.

If the blood pressure monitor is equipped only with a unidirectional transmission function, the state of the portable information terminal (e.g., the data reception status) cannot be referred to from the blood pressure monitor. Thus, there is a risk that the portable information terminal may fail to receive the blood pressure data. A case is assumed, for example, where blood pressure data obtained by multiple measurements is divided into a plurality of items of divisional data, which are then transmitted in a plurality of advertisement packets. In such a case, part of the blood pressure data obtained by the multiple measurements may end up being lost and abandoned.

By allowing the portable information terminal to temporarily stay approximately still in the proximity of the blood pressure monitor, the portable information terminal becomes capable of stably receiving the blood pressure data transmitted from the blood pressure monitor, thereby preventing the blood pressure data from being lost. However, blood pressure data may continue to be lost due to variations in behavior patterns of the user who owns the portable information terminal.

An object of the present invention is to provide a technique for preventing a decrease in the degree of confidentiality of specific data transmitted through unidirectional communications, and reducing the possibility of reception failures.

According to a first aspect of the invention, a data transmitting apparatus comprises an input unit that selectively accepts a first user input and a second user input, the first user input instructing transmission of first data, the second user input temporarily switching from transmission of the first data to transmission of second data, a transmission control unit that instructs, based on the first user input, transmission of a first packet, and temporarily instructs, based on the second user input, transmission of a second packet in place of the instruction to transmit the first packet, the first packet containing the first data, the second packet containing the second data, and a transmitting unit that transmits the first packet through a unidirectional communication based on the instruction to transmit the first packet, and that transmits the second packet through a unidirectional communication based on the instruction to transmit the second packet.

According to the data transmitting apparatus of the first aspect, transmission of a first packet is instructed based on a first user input, and the first packet is transmitted through a unidirectional communication based on the instruction to transmit the first packet. It is thereby possible to transmit first data to a data receiving apparatus capable of receiving the first packet, without the need for pairing or complicated communication procedures. Moreover, according to the data transmitting apparatus, transmission of a second packet containing second data is temporarily instructed, in place of the instruction to transmit the first packet, based on a second user input, and the second packet is transmitted through a unidirectional communication based on the instruction to transmit the second packet. It is thereby possible to temporarily transmit the second data to a data receiving apparatus capable of receiving the second packet, without the need for pairing or complicated communication procedures. Since the second data is temporarily transmitted, a high degree of confidentiality of the second data can be ensured, as compared to the first data. Furthermore, since the user who owns the data receiving apparatus approaches the data transmitting apparatus and executes the second user input (operation), the data receiving apparatus approaches the data transmitting apparatus and temporarily stays approximately still, which allows the data receiving apparatus to stably receive the second data from the data transmitting apparatus, thus reducing the possibility of failure to receive the second data transmitted through a unidirectional communication.

According to a second aspect of the invention, the first data includes transmission-related information related to transmission of biological data.

According to the data transmitting apparatus of the second aspect, it is possible to transmit transmission-related information to a data receiving apparatus capable of receiving a first packet, without the need for pairing or complicated, communication procedures, and to provide the transmission-related information to a user who owns the data receiving apparatus capable of receiving the first packet. The user who has been provided with the transmission-related information is capable of recognizing the transmission-related information.

According to a third aspect of the invention, the transmission-related information includes transmission history information of the biological data.

According to the data transmitting apparatus of the third aspect, it is possible to transmit transmission history information to a data receiving apparatus capable of receiving a first packet, without the need for pairing or complicated communication procedures, and to provide the transmission history information to a user who owns the data receiving apparatus capable of receiving the first packet. The user who has been provided with the transmission history information is capable of recognizing the transmission history information.

According to a fourth aspect of the invention, the transmission-related information includes support information that guides an operation to transmit the biological data.

According to the data transmitting apparatus of the fourth aspect, it is possible to transmit support information to a data receiving apparatus capable of receiving a first packet, without the need for pairing or complicated communication procedures, and to provide the support information to a user who owns the data receiving apparatus capable of receiving the first packet. The user who has been provided with the support information can recognize the necessity of the operation for transmitting biological data to the data transmitting apparatus.

According to a fifth aspect of the invention, the second data includes the biological data.

According to the data transmitting apparatus of the fifth aspect, it is possible to transmit biological data to a data receiving apparatus capable of receiving a first packet, without the need for pairing or complicated communication procedures. Moreover, since the second data includes biological data, and is temporarily transmitted, a high degree of confidentiality of the biological data can be ensured, as compared to the first data. Furthermore, since the user who owns the data receiving apparatus approaches the data transmitting apparatus and executes the second user input (operation), the data receiving apparatus approaches the data transmitting apparatus and temporarily stays approximately still, which allows the data receiving apparatus to stably receive the biological data from the data transmitting apparatus, thus reducing the possibility of failure to receive the biological data transmitted through a unidirectional communication.

According to the present invention, it is possible to provide a technique for preventing a decrease in the degree of confidentiality of specific data transmitted through unidirectional communications, and reducing the possibility of reception failures.

DETAILED DESCRIPTION

Figure 1:
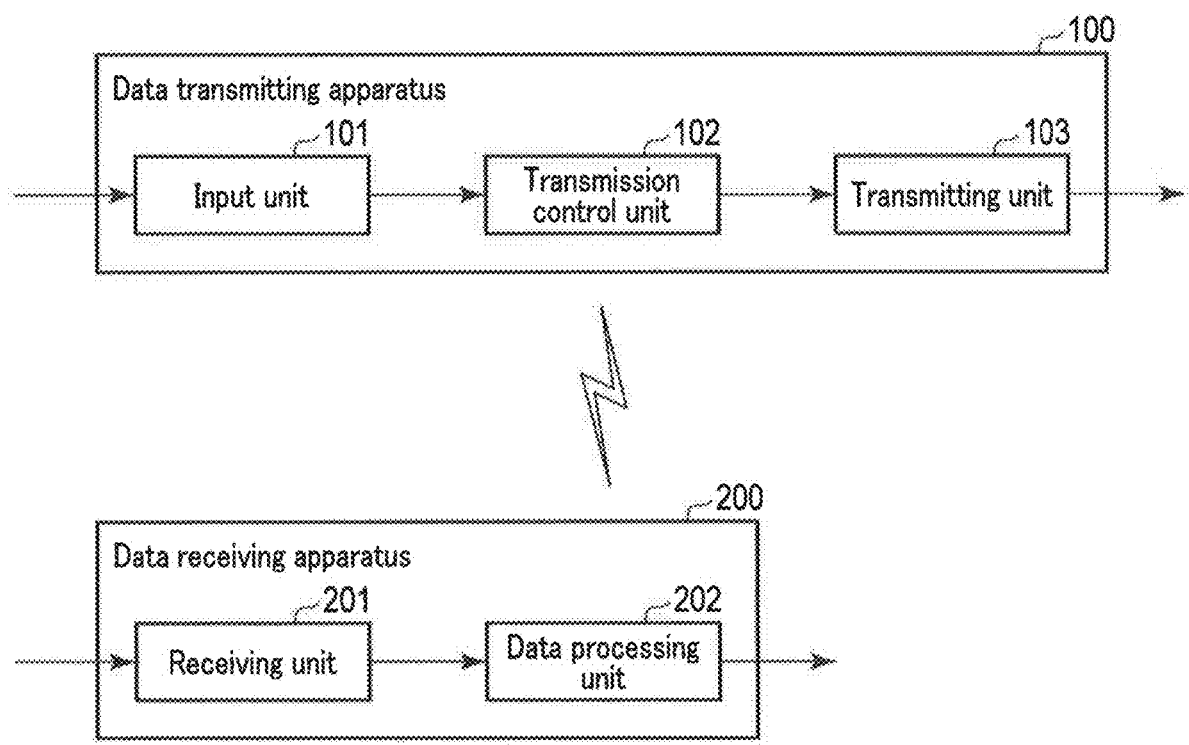
FIG. 1 is a diagram schematically showing an application example of a data transmission and reception system according to the present embodiment.

Hereinafter, an embodiment according to an aspect of the present invention (also referred to as "the present embodiment" hereinafter) will be described, with reference to the drawings.

Elements that are the same as or similar to elements already described will be denoted by the same or similar reference numerals, and redundant descriptions will be basically omitted.

§1 APPLICATION EXAMPLE

An application example of the present invention will be described, with reference to FIG. 1. FIG. 1 schematically shows an application example of a data transmission and reception system according to the present embodiment. As shown in FIG. 1, the data transmission and reception system includes a data transmitting apparatus 100 and a data receiving apparatus 200.

The data transmitting apparatus 100 includes at least an input unit 101, a transmission control unit 102, and a transmitting unit 103.

The input unit 101 accepts a user input that instructs the data transmitting apparatus of various operations. For example, the input unit 101 accepts a first user input, which instructs transmission of first data that is not confidential (the first data will also be referred to as "non-confidential data" hereinafter). The first user input instructs commencement of transmission of the first data, and also instructs continuation of the transmission of the first data. The first user input may be an input including commencement of operation. That is, the first user input instructs commencement of the supply of a power-supply voltage, commencement of transmission of the first data, and continuation of the transmission of the first data. The input unit 101 accepts a second user input, which temporarily switches from the transmission of the first data to transmission of second data that is confidential (the second data will also be referred to as "confidential data" hereinafter). The input unit 101 accepts a third user input, which instructs termination of the operation. The termination of the operation means terminating the transmission of the first data if the first data is being transmitted, and terminating the transmission of the second data if the second data is being transmitted. The termination of the operation may mean both terminating the transmission of the first or second data and terminating the supply of the power-supply voltage.

The transmission control unit 102 instructs, based on the first user input, execution of transmission of a first packet containing the first data. For example, the transmission control unit 102 instructs, based on the first user input, repeated transmission of the first packet over a period of time until the second or third user input is accepted. The first data includes, for example, transmission-related information related to transmission of biological data. The transmission-related information includes at least one of transmission history information on biological data and support information that guides the operation for transmitting the biological data. The transmission history information includes at least one of information on the presence or absence of yet-to-be-transmitted biological data, and information on the number of items of yet-to-be-transmitted biological data. The support information includes an operation procedure, etc. for causing the data transmitting apparatus 100 to transmit the second data. The operation procedure includes, for example, information indicating that transmission of biological data is commenced by a second user input to the input unit 101 of the data transmitting apparatus 100. The user can recognize, from the support information, that transmission of biological data is commenced by the transmitting unit 103 of the data transmitting apparatus 100 via the second user input to the input unit 101 of the data transmitting apparatus 100.

The first data may be substantially meaningful data as described above, or may be substantially meaningless data (Null).

Based on the second user input, the transmission control unit 102 temporarily instructs execution of transmission of the second packet containing the second data, in place of the execution of the transmission of the first packet containing the first data. Based on the second user input subsequent to the first user input, the transmission control unit 102 instructs repeated transmission of the second packet over a predetermined period of time (e.g., a designated period of time ranging from one to sixty seconds), and instructs repeated transmission of the first packet subsequent to passage of the predetermined period of time. Alternatively, the transmission control unit 102 may be configured to instruct repeated transmission of the second packet over a period of time until the first or third user input is accepted, based on the second user input subsequent to the first user input. For example, the second data includes biological data and date-and-time data associated with the biological data, and the biological data includes blood pressure data.

The second data may be transmitted in a plurality of second packets by dividing the second data to be transmitted into a plurality of items of divisional data, and storing the plurality of items of second data in data fields of the plurality of second packets. This is effective in the case where the second data does not fit in the data field of a single second packet. For example, when second data to be transmitted is divided into N items of divisional data (where N is an integer equal to or greater than 2) and the second data is transmitted in N second packets, the transmission control unit 102 instructs repeated transmission of a single packet group consisting of N second packets, based on a second user input.

The first data to be transmitted need not be divided into a plurality of items of divisional data, and may be transmitted in a single packet; alternatively, the first data may be transmitted in a plurality of first packets by dividing the first data to be transmitted into a plurality of items of divisional data, and storing the plurality of items of divisional data in data fields of the plurality of first packets. For example, when the first data to be transmitted is divided into N items of divisional data (where N is an integer equal to or greater than 2) and the first data is transmitted in N first packets, the transmission control unit 102 instructs repeated transmission of a single packet group consisting of N first packets, based on the first user input.

The transmitting unit 103 transmits, through a unidirectional communication compliant with a communication standard such as BLE, a radio signal that carries a packet defined by the standard. Based on an instruction to repeatedly transmit the first packet, for example, the transmitting unit 103 repeatedly transmits a first packet for unidirectional communications. The transmitting unit 103 transmits a second packet for unidirectional communications based on an instruction to transmit the second packet.

As shown in FIG. 1, the data receiving apparatus 200 includes at least a receiving unit 201 and a data processing unit 202. The receiving unit 201 receives a radio signal that carries the first and second packets for unidirectional communications from the data transmitting apparatus 100. The receiving unit 201 sends the reception signal to the data processing unit 202.

The data processing unit 202 fetches a first packet from the reception signal, fetches first data from the first packet, and outputs the fetched first data. The data processing unit 202 fetches a second packet from the reception signal, fetches second data from the second packet, and outputs the fetched second data.

For example, transmission-related information can be displayed, based on the first data, on a display unit, etc. to which the first data is output. If, for example, the transmission-related information includes the transmission history information, and the transmission history information includes information on the presence or absence of yet-to-be-transmitted biological data and the numbers for yet-to-be-transmitted biological data, the user of the data receiving apparatus 200 can recognize, from the displayed information, the presence or absence of yet-to-be-transmitted biological data and the number of items of yet-to-be-transmitted biological data. If the transmission-related information, includes support information and the support information includes an operation method, etc. for causing the data transmitting apparatus 100 to transmit the second data, the user of the data receiving apparatus 200 can recognize, from the displayed information, the operation method, etc. for causing the data transmitting apparatus 100 to transmit the second data. The aforementioned trigger an operation on the data transmitting apparatus 100 (via a second user input to the input unit 101), causing a second packet to be transmitted from the transmitting unit 103 of the data transmitting apparatus 100, and received by the data receiving apparatus 200. Thereby, the second data (biological data) contained in the second packet is acquired.

In this manner, in the data transmitting apparatus 100, the supply of the power-supply voltage, for example, is commenced based on the first user input, and transmission of non-confidential data is commenced through a unidirectional communication and continued; however, transmission of confidential data is not commenced. When one or more data receiving apparatuses 200 enter the communication area of the data transmitting apparatus 100, the data receiving apparatuses 200 that have entered the communication area receive non-confidential data, but do not receive confidential data at this point in time; therefore, the leakage of the confidential data does not occur.

Of users who own the data receiving apparatuses 200, those who are not conscious of receiving confidential data (hereinafter also referred to as "non-target users") generally do not remain in the communication area of the data transmitting apparatus 100; such users tend to move away from the apparatus or leave the area. Non-target users are not conscious of the operation on the data transmitting apparatus 100 or the displayed contents of the data transmitting apparatus 100, and therefore tend not to approach the data transmitting apparatus 100. In this case, the data receiving apparatus 200 owned by the non-target users (hereinafter also referred to as "non-target data receiving apparatus 200") tends not to approach the data transmitting apparatus 100 and subsequently stay still, and the environment of communications between the data transmitting apparatus 100 and the non-target data receiving apparatus 200 is apt to be unstable, increasing the likelihood of the loss of received data.

On the other hand, of users who own the data receiving apparatus 200, those who desire to receive confidential data (hereinafter also referred to as "target users") are assumed to approach the data transmitting apparatus 100, temporarily stay approximately still, and execute a second user input to the data transmitting apparatus 100. One of the causes of such a behavioral action is the target user's viewing of the support information displayed by the data receiving apparatus 200 (hereinafter also referred to as "target data receiving apparatus 200") owned by the target user himself or herself. Since the target user who has viewed the support information at least once in the past is assumed to trigger the above-described behavior, the target data receiving apparatus 200 need not constantly and stably receive non-confidential data including support information. Based on the second user input, the data transmitting apparatus 100 transmits confidential data over a predetermined period of time, terminates the transmission of the confidential data subsequent to passage of the predetermined period of time, and recommences the transmission of the non-confidential data. The target user is assumed to approach the data transmitting apparatus 100 and temporarily stay approximately still for such a limited period of time, and the environment of communications between the data transmitting apparatus 100 and the target data receiving apparatus 200 becomes favorable. This allows the target data receiving apparatus 200 to stably receive confidential data. This reduces or prevents the loss of confidential data.

The non-target data receiving apparatus 200, which is unlikely to approach the data transmitting apparatus 100 and stay still in such a limited period of time, is unlikely to receive confidential data. On the other hand, the target data receiving apparatus 200, which is assumed to approach the data transmitting apparatus 100 and temporarily stay approximately still in such a limited period of time, is capable of stably receiving confidential data. This reduces the possibility of a leakage of confidential data occurring.

In the above-described manner, the data transmitting apparatus 100 is capable of providing data transmission technology for reducing the possibility of failure to receive specific data (confidential data) transmitted through unidirectional communications. Also, the data transmitting apparatus 100 is capable of reducing the possibility of a leakage of specific data occurring.

§2 CONFIGURATION EXAMPLE

<Data Transmission and Reception System>

Figure 2:
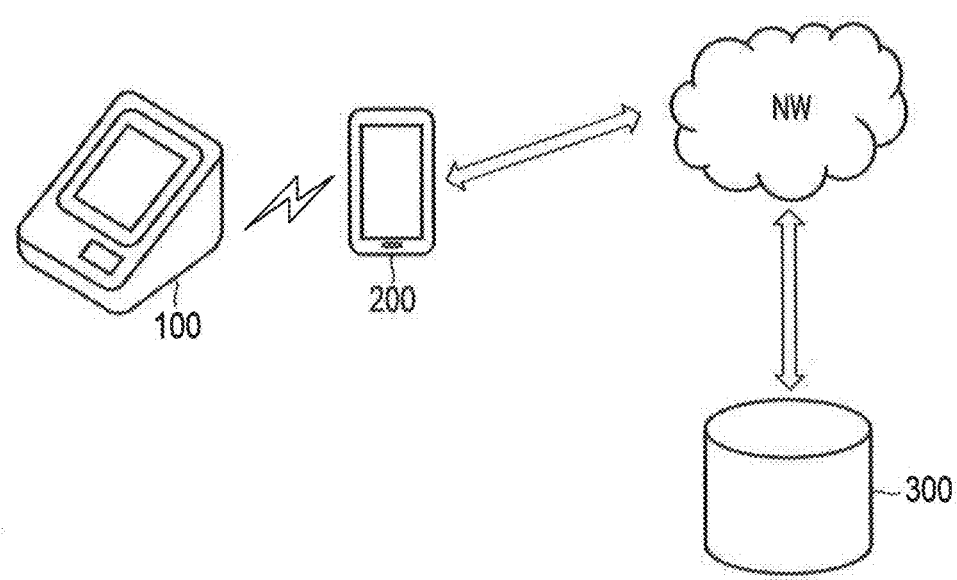
FIG. 2 is a conceptual diagram illustrating a data transmission and reception system including a data transmitting apparatus and a data receiving apparatus according to the present embodiment.

An example of the data transmission and reception system according to the present embodiment will be described, with reference to FIG. 2. FIG. 2 is a conceptual diagram illustrating a data transmission and reception system including the data transmitting apparatus 100 and the data receiving apparatus 200 according to the present embodiment.

The data transmitting apparatus 100 is a sensor device that routinely measures an amount related to biological information or activity information of the user, such as a blood pressure monitor, a thermometer, an activity tracker, a pedometer, a body composition scale, and a weight scale. The data transmitting apparatus 100 is a device that allows for unidirectional communications such as BLE. In the example of FIG. 2, the appearance of a stationary blood pressure monitor is shown as the data transmitting apparatus 100; however, the data transmitting apparatus 100 is not limited thereto, and may be a wrist watch-type wearable blood pressure monitor, or other sensor device that measures the amount related to biological information or activity information. The data transmitting apparatus 100 transmits, through unidirectional communications, measurement data indicating an amount related to biological information or activity information. It is to be noted that the measurement data corresponds to the transmission data.

The data receiving apparatus 200 is a portable information terminal such as a smartphone or a tablet. The data receiving apparatus 200 is an apparatus that allows for wireless communications, such as BLE, mobile communications (3G, 4G, etc.), and WLAN.

The data receiving apparatus 200 receives transmission data transmitted from the data transmitting apparatus 100 through unidirectional communications such as BLE. The data receiving apparatus 200 transmits the transmission data to the data server 300 via a network. The data receiving apparatus 200 employs, for example, mobile communications or WLAN.

The data server 300 corresponds to a database that manages, based on the transmission data, biological information or activity information of a large number of users.

<Data Transmitting Apparatus>

[Hardware Configuration]

Figure 3:
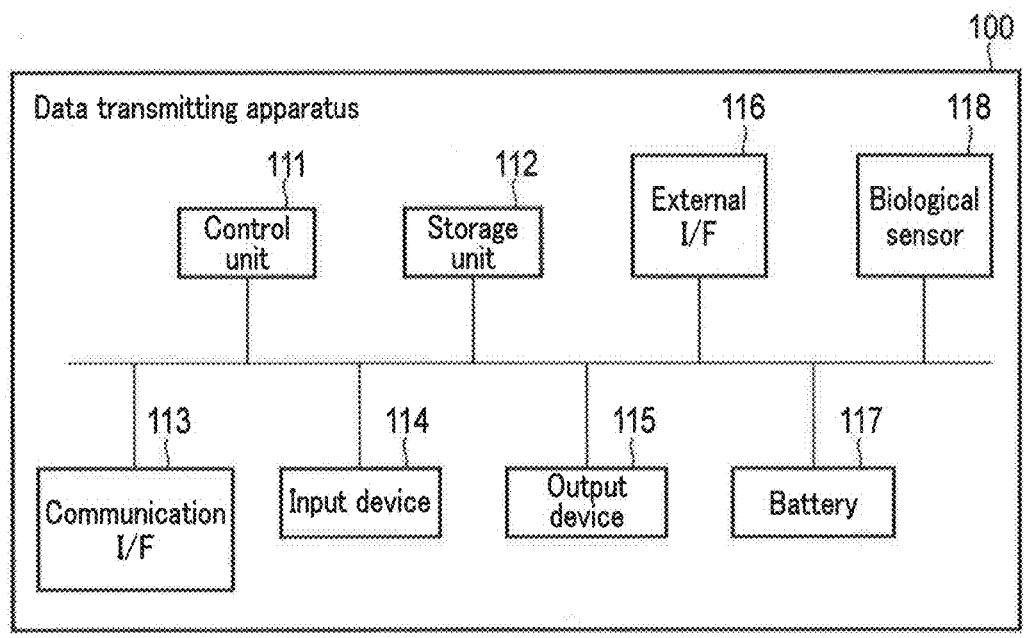
FIG. 3 is a block diagram showing an example of a hardware configuration of the data transmitting apparatus according to the present embodiment.

Next, an example of a hardware configuration of the data transmitting apparatus 100 according to the present embodiment will be described, with reference to FIG. 3. FIG. 3 schematically shows an example of a hardware configuration of the data transmitting apparatus 100 according to the present embodiment.

As shown in FIG. 3, the data transmitting apparatus 100 is a computer in which a control unit 111, a storage unit 112, a communication interface 113, an input device 114, an output device 115, an external interface 116, a battery 117, and a biological sensor 118 are electrically connected. In FIG. 3, the communication interface and the external interface are respectively denoted as "communication I/F" and "external I/F".

The control unit 111 includes a central processing unit (CPU), a random access memory (RAM), a read-only memory (ROM), etc. The CPU is an example of a processor. The CPU expands a program stored in the storage unit 112 into the RAM. When the CPU interprets and executes the program, the control unit 111 becomes capable of executing various information processing operations, such as the processing of functional blocks, which will be described below in item "Software Configuration".

The storage unit 112 is a so-called auxiliary storage device, and may he, for example, a semiconductor memory such as a built-in or external flash memory, a hard disk drive (HDD), or a solid-state drive (SSD). The storage unit 112 stores programs to be executed by the control unit 111, data to be used by the control unit 111, etc. Programs can also be referred to as instructions for operating the control unit 111.

The communication interface 113 includes at least a wireless module that transmits (advertises) a packet through a unidirectional communication such as BLE. The BLE advertising will be described later. The wireless module receives, from the control unit 111, an advertisement packet in BLE in which the transmission data is stored. The wireless module transmits an advertisement packet. The wireless module is also referred to as a "transmitting unit". It is to be noted that, in the future, BLE may be replaced by other communication standards that allow for low power consumption and unidirectional communications. In that case, the following description may be suitably varied.

The input device 114 is a device for accepting user inputs made via a touch screen, buttons, switches, etc.

The output device 115 is, for example, a device for making outputs from a display, a speaker, etc.

The external interface 116 is a Universal Serial Bus (USE) port, a memory card slot, etc., and is an interface for connection to an external device.

The battery 117 supplies a power-supply voltage for the data transmitting apparatus 100. The battery 117 may be replaceable. It is to be noted that the data transmitting apparatus 100 may be connectable to a commercial power supply via an alternating-current (AC) adapter. In this case, the battery 117 can be omitted.

The biological sensor 118 obtains measurement data by measuring an amount related to the user's biological information. The operation of the biological sensor 118 is controlled by, for example, an unillustrated sensor controller. The measurement data is stored in the storage unit 112 in association with the date-and-time data. The biological sensor 118 typically includes a blood pressure sensor that obtains blood pressure data by measuring an amount related to the user's blood pressure. In this case, the measurement data includes blood pressure data. The blood pressure data may include, for example, values of the systolic blood pressure (SBP) and the diastolic blood pressure (DBP), as well as the pulse rate, but is not limited thereto. In addition, the measurement data can include electrocardiogram data, pulse wave data, body temperature data, etc.

The blood pressure sensor can include a blood pressure sensor (hereinafter also referred to as a "continuous blood pressure sensor") capable of continuously measuring an amount related to the user's blood pressure per beat. The continuous blood pressure sensor may continuously measure an amount related to the use blood pressure from a pulse transit time (PTT), or may implement continuous measurement by the tonometry technique or other techniques.

The blood pressure sensor may include a blood pressure sensor that cannot perform continuous measurements (hereinafter also referred to as a "discontinuous blood pressure) sensor"), in place of or in addition to the continuous blood pressure sensor. A discontinuous blood pressure sensor measures an amount related to a user's blood pressure using, for example, a cuff as a pressure sensor (oscillometric method).

A discontinuous blood pressure sensor (in particular, an oscillometric blood pressure sensor) tends to provide higher measurement accuracy than a continuous blood pressure sensor. Thus, the blood pressure sensor may be configured to measure the blood pressure data with high precision, triggered by satisfaction of a certain condition (e.g., the user's blood pressure data obtained by measurement of the continuous blood pressure sensor indicates a predetermined state), by operating a discontinuous blood pressure sensor in place of a continuous blood pressure sensor.

It should be noted that, regarding the specific hardware configuration of the data transmitting apparatus 100, the components can be suitably omitted, replaced, or added, according to the embodiment. The control unit 111 may include, for example, a plurality of processors. The data transmitting apparatus 100 may be configured from a plurality of sensor devices.

[Software Configuration]

Figure 4:
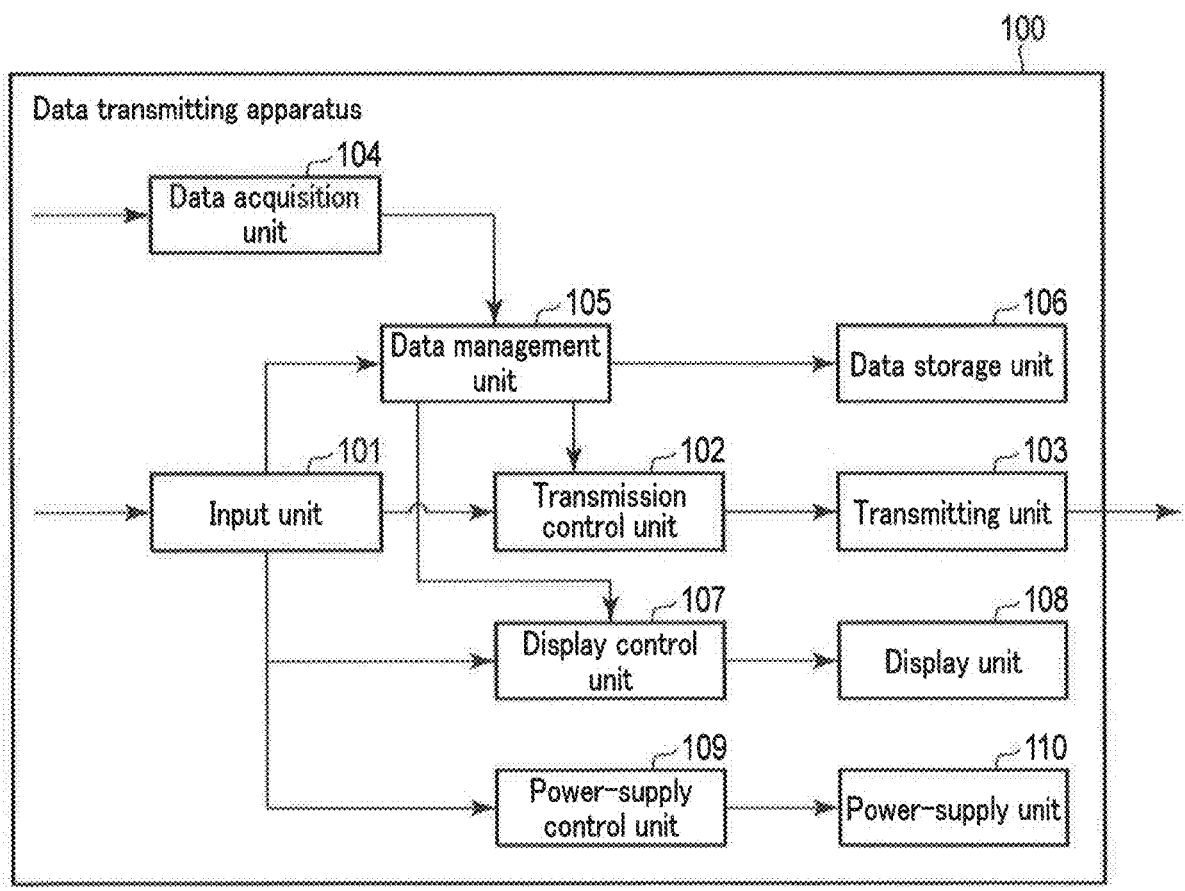
FIG. 4 is a block diagram showing an example of a software configuration of the data transmitting apparatus according to the present embodiment.

Next, an example of a software configuration of the data transmitting apparatus 100 according to the present embodiment will be described, with reference to FIG. 4. FIG. 4 schematically shows an example of a software configuration of the data transmitting apparatus 100.

The control unit 111 in FIG. 3 expands the program stored in the storage unit 112 into the RAM. Thereafter, the control unit 111 causes the CPU to interpret and execute the program, and controls various hardware elements shown in FIG. 3. Thereby, as shown in FIG. 4, the data transmitting apparatus 100 functions as a computer including an input unit 101, a transmission control unit 102, a transmitting unit 103, a data acquisition unit 104, a data management unit 105, a data storage unit 106, a display control unit 107, a display unit 108, a power-supply control unit 109, and a power-supply unit 110.

The data acquisition unit 104 acquires biological data output from the biological sensor 118, and outputs the acquired biological data to the data management unit 105.

The data management unit 105 receives the biological data, and writes the received biological data into the data storage unit 106. The data management unit 105 generates, based on a first user input, a first packet containing first data, and inputs the first packet to the transmission control unit 102. Also, the data management unit 105 generates, based on a second user input, a second packet containing second data, and inputs the second packet to the transmission control unit 102. The first data includes, for example, transmission-related information related to transmission of biological data. The second data includes biological data and date-and-time data associated with the biological data. A configuration may be adopted in which the transmission control unit 102 generates a first packet in advance regardless of a first user input, the data storage unit 106 stores data in the first packet, and the transmission control unit 102 reads, based on the first user input, the first packet from the data storage unit 106 to allow the first packet to be input to the transmission control unit 102. Similarly, a configuration may be adopted in which the transmission control unit 102 generates a second packet in advance, regardless of a second user input, the data storage unit 106 stores data in the second packet, and the transmission control unit 102 reads, based on the second user input, the second packet from the data storage unit 106 to allow the second packet to be input to the transmission control unit 102.

The data management unit 105 manages a plurality of first packets and a plurality of second packets by distinguishing between packets transmitted and packets yet to he transmitted through unidirectional communications. Each packet contains unique identification information, and the data management unit 105 manages the transmitted packets and the yet-to-be-transmitted packets in association with the unique identification information. This allows the data management unit 105 to manage the number of first packets transmitted, the number of first packets yet to be transmitted, the number of second packets transmitted, and the number of second packets yet to be transmitted.

The data management unit 105 may read the biological data stored in the data storage unit 106, triggered by an instruction from the transmission control unit 102 or the display control unit 107, and transmits the biological data to the transmission control unit 102 or the display control unit 107.

The data storage unit 106 stores biological data written by the data management unit 105. The data storage unit 106 stores the first and second packets written by the data management unit 105. When biological data is newly stored, the data management unit 105 may automatically send the biological data to the display control unit 107.

The input unit 101 selectively accepts some user inputs. For example, the input unit 101 accepts a first user input that instructs transmission of first data, and sends the first user input to the transmission control unit 102, etc. The input unit 101 accepts a second user input that temporarily switches from transmission of the first data to transmission of the second data, and sends the second user input to the transmission control unit 102, etc. The input unit 101 accepts a third user input that instructs termination of the operation, and sends the second user input to the transmission control unit 102, etc. The input unit 101 accepts a fourth user input that controls data display on the display unit 108 and a fifth user input that instructs commencement of measurement by the biological sensor 118.

Based on the first user input, the transmission control unit 102 instructs commencement of transmission of the first data, instructs continuation of transmission of the first data, and inputs the generated first packet or the first packet read from the data storage unit 106 to the transmitting unit 103. For example, the transmission control unit 102 instructs, based on the first user input, repeated transmission of the first packet over a period of time until the second or third user input is accepted. Based on the second user input, the transmission control unit 102 temporarily switches from transmission of the first data to transmission of the second data, and inputs the generated second packet or the second packet read from the data storage unit 106 to the transmitting unit 103. Based on the second user input subsequent to the first user input, the transmission control unit 102 instructs repeated transmission of the second packet over a predetermined period of time, and instructs repeated transmission of the first packet subsequent to passage of the predetermined period of time. Alternatively, the transmission control unit 102 may be configured to instruct repeated transmission of the second packet over a period of time until the first or third user input is accepted, based on the second user input subsequent to the first user input.

In the case of instructing execution of transmission of the first packet, the transmission control unit 102 notifies the data management unit 105 of unique identification information of the first packet, and the data management unit 105 manages, based on the notification, the transmitted first packet as having been transmitted. Similarly, in the case of instructing execution of transmission of the second packet, the transmission control unit 102 notifies the data management unit 105 of unique identification information of the second packet, and the data management unit 105 manages, based on the notification, the transmitted second packet as having been transmitted.

The transmitting unit 103 transmits, through a unidirectional communication compliant with a communication standard such as BLE, a radio signal that carries a packet defined by the standard. Based on an instruction to repeatedly transmit the first packet, for example, the transmitting unit 103 repeatedly transmits (advertises) a first packet for unidirectional communications. The transmitting unit 103 transmits a second packet for unidirectional communications based on an instruction to transmit the second packet.

The display control unit 107 generates display data based on the user input from the input unit 101 and the data from the data management unit 105, and inputs the generated display data to the display unit 108. The display unit 108 displays an image based on display data input from the display control unit 107.

For example, the display control unit 107 reads, based on the fourth user input, biological data from the data storage unit 106, generates display data for the display unit 108 based on the read biological data, and the display unit 108 then displays an image corresponding to the biological data based on the generated display data. The display control unit 107 generates, based on the first user input, display data for the display unit 108, and the display unit 108 then displays, based on the generated display data, an image corresponding to guidance to transmit the first data and an image corresponding to the support information. The display control unit 107 generates, based on the second user input, display data for the display unit 108, and the display unit 108 then displays, based on the generated display data, an image corresponding to the guidance to transmit the second data.

The power-supply control unit 109 instructs, based on the first user input from the input unit 101, commencement of the supply of the power-supply voltage, and instructs, based on the third user input from the input unit 101, termination of the supply of the power-supply voltage.

The power-supply unit 110 commences the supply of the power-supply voltage based on the instruction to commence supply of the power--supply voltage from the power-supply control unit 109, and terminates the supply of the power-supply voltage based on the instruction to terminate the supply of the power-supply voltage from the power-supply control unit 109.

<Data Receiving Apparatus>
[Hardware Configuration]

Figure 5:
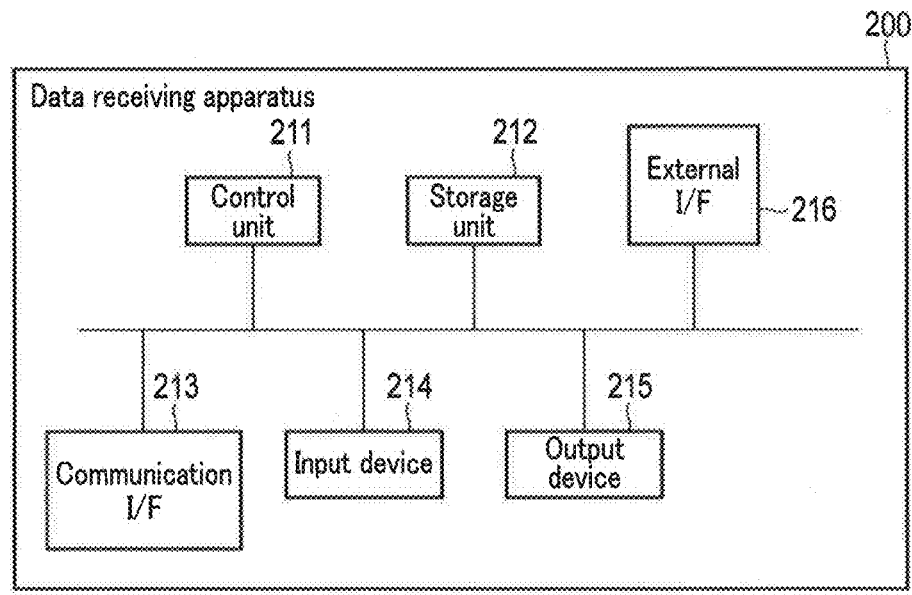
FIG. 5 is a block diagram showing an example of a hardware configuration of the data receiving apparatus according to the present embodiment.

Next, an example of a hardware configuration of the data receiving apparatus 200 according to the present embodiment will be described, with reference to FIG. 5. FIG. 5 schematically shows an example of the hardware configuration of the data receiving apparatus 200.

As shown in FIG. 5, the data receiving apparatus 200 is a computer in which a control unit 211, a storage unit 212, a communication interface 213, an input device 214, an output device 215, and an external interface 216 are electrically connected. In FIG. 5, the communication interface and the external interface are respectively denoted as "communication I/F" and "external I/F".

The control unit 211 includes a CPU, a RAM, a ROM, etc. The CPU is an example of a processor. The CPU expands the program stored in the storage unit 212 into the RAM. When the CPU interprets and executes this program, the control unit 211 can execute various information processing operations, such as the processes of functional blocks to be described in item "Software Configuration".

The storage unit 212 is a so-called auxiliary storage device, and may be, for example, a semiconductor memory such as a built-in or external flash memory. The storage unit 212 stores programs to be executed by the control unit 211, data to be used by the control unit 211, etc. Programs can also be referred to as instructions for operating the control unit 211.

The communication interface 213 includes various wireless communication modules, which are mainly for BLE, mobile communications (e.g., 3G and 4G), WLAN, etc. The communication interface 213 may further include a wired communication module such as a wired local area network (LAN) module. The communication module for BLE receives, from the data transmitting apparatus 100, an advertisement packet, etc. in which measurement data is stored. The communication module for BLE may also be referred to as a "receiving unit".

The input device 214 is a device for accepting a user input such as a touch screen.

The output device 215 is a device for making outputs from, for example, a display, a speaker, etc.

The external interface 216 is a USE port, a memory card slot, etc., and is an interface for connection to an external device.

It should be noted that, regarding the specific hardware configuration of the data receiving apparatus 200, the components can be suitably omitted, replaced, or added, according to the embodiment. For example, the control unit 211 may include a plurality of processors. The data receiving apparatus 200 may be configured of a plurality of information processing devices. As the data receiving apparatus 200, a general-purpose tablet personal computer (PC), etc., as well as an information processing device designed exclusively for the services to be provided, may be used.

[Software Configuration]

Figure 6:
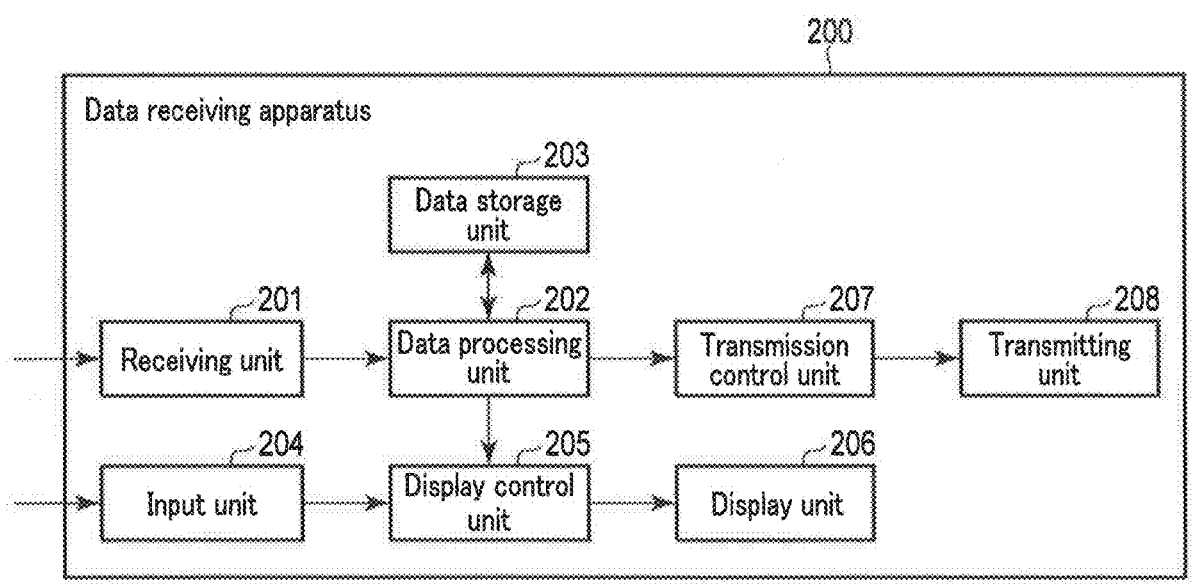
FIG. 6 is a block diagram showing an example of a software configuration of the data receiving apparatus according to the present embodiment.

Next, an example of a software configuration of the data receiving apparatus 200 according to the present embodiment will be described, with reference to FIG. 6. FIG. 6 schematically shows an example of a software configuration of the data receiving apparatus 200.

The control unit. 211 in FIG. 5 expands the program stored in the storage unit 212 into the RAM. Thereafter, the control unit 211 causes the CPU to interpret and execute the program, and controls various hardware elements shown in FIG. 5. Thereby, as shown in FIG. 6, the data receiving apparatus 200 functions as a computer including a receiving unit 201, a data processing unit 202, a data storing unit 203, an input unit 204, a display control unit 205, a display unit: 206, a transmission control unit 207, and a transmitting unit 208.

The receiving unit 201 receives a radio signal that carries a packet from the data transmitting apparatus 100. This packet is, for example, an advertisement packet in BLE. It is to be noted that, in the future, BLE may be replaced by other communication standards that allow for low power consumption and unidirectional communications. In that case, the following description may be suitably varied.

A schematic description of BLE advertisement will be given below.

Figure 7:
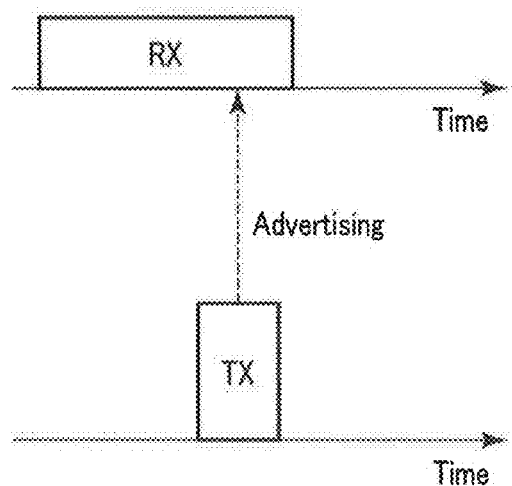
FIG. 7 is a diagram illustrating advertising performed in BLE.

In the passive scanning mode adopted in BLE, a new node periodically transmits advertisement packets to indicate its presence, as illustrated in FIG. 7. By entering a sleep state, which consumes only a low amount of power, during the period from transmission of an advertisement packet to transmission of a subsequent advertisement packet, the new node can conserve power consumption. Since the receiver sides of advertisement packets also operate intermittently, the power consumption incurred in transmission and reception of advertisement packets is low.

Figure 8:
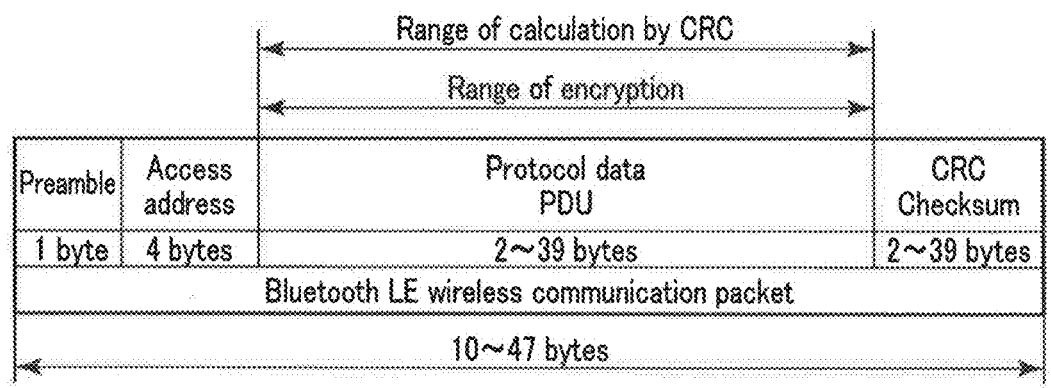
FIG. 8 is a diagram illustrating a data structure of a packet transmitted and received in BLE.

FIG. 8 shows a basic configuration of a BLE wireless communication packet. A BLE wireless communication packet contains a 1-byte preamble, a 4-byte Access Address, a 2-to-39-byte (variable) Protocol Data Unit (PDU), and a 3-byte Cyclic Redundancy Checksum (CRC). The length of the BLE wireless communication packet depends on the length of the PDU, and ranges from 10 to 47 bytes. A 10-byte BLE wireless communication packet (with a 2-byte PDU) is also called an Empty PDU packet, and is periodically exchanged between the master and the slave.

The preamble field is prepared for synchronization in BLE wireless communications, and stores repetitions of "01" or "10". As the Access Address, fixed numerical values are stored in an advertising channel, and random numbers are stored in the data channel. In the present embodiment, an advertisement packet that is a BLE wireless communication packet transmitted on the advertising channel is targeted. The CRC field is used for detection of reception errors. The range of calculation by the CRC is only the PDU field.

Figure 9:
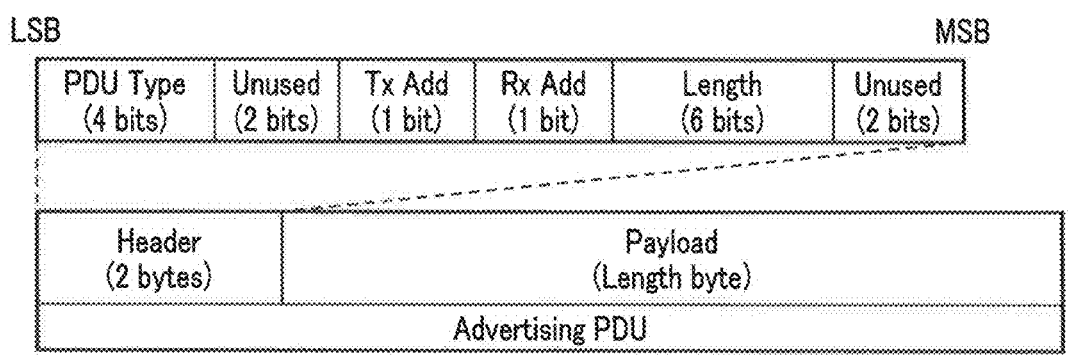
FIG. 9 is a diagram illustrating a data structure of a PDU field in an advertisement packet.

Next, the PDU field of the advertisement packet will be described, with reference to FIG. 9.

The PDU field of the advertisement packet contains a 2-byte header and a 0-to-37-byte (variable) payload. The header further includes a 4-bit PDU Type field, a 2-bit unused field, a 1-bit TxAdd field, a 1-bit RxAdd field, a 6-bit Length field, and a 2-bit unused field.

A value indicating the type of the PDU is stored in the PDU Type field. Some values such as "connectable advertising" and "non-connectable advertising" have been defined. A flag indicating whether or not a transmission address is present in the payload is stored in the TxAdd field. Similarly, a flag indicating whether or not a reception address is present in the payload is stored in the RxAdd field. In the Length field, a value indicating the byte size of the payload is stored.

The payload can store given data. Accordingly, the data transmitting apparatus 100 stores the biological data and the date-and-time data in the payload using a predetermined data structure. The data structure may include, for example: an identifier indicating the user; an identifier indicating the data transmitting apparatus 100 from which the data is transmitted; an identifier indicating the data receiving apparatus 200 for which the data is destined; the date-and-time data; and one or more types of measurement data such as the systolic blood pressure and the diastolic blood pressure associated with the date-and-time data, the pulse rate, and the amount of activity.

Returning to the description of the software configuration of the data receiving apparatus 200, the receiving unit 201 performs reception processing including low-noise amplification, filtering, down-conversion, etc. on a radio signal, and obtains a reception signal in the intermediate frequency bandwidth or the baseband bandwidth. The receiving unit 201 sends the reception signal to the data processing unit 202.

The data processing unit 202 reproduces a BLE advertisement packet transmitted from the data transmitting apparatus 100 by performing demodulation and decoding on the reception signal. Thereafter, the data processing unit 202 extracts the PDU payload from the BLE advertisement packet.

By checking, for example, the identifier (indicating the apparatus from which the measurement data is transmitted or the valid destination) contained in the payload, the data processing unit 202 may discard the received packet if the value of the identifier is inappropriate. If the value of the identifier is appropriate, the data processing unit 202 inputs the first or second data extracted from the BLE advertisement packet to the display control unit 205, and inputs the first data extracted from the BLE advertisement packet to the data storing unit 203.

The data storing unit 203 stores the date-and-time data and the biological data included in the first data in association with each other, and outputs the stored date-and-time data and biological data upon receipt of a read request.

In accordance with an instruction from, for example, an unillustrated high-order application (e.g., an application that manages biological data), the data processing unit 202 reads a set of date-and-time data and biological data stored in the data storing unit 203, and inputs the read set of data to the display control unit 205 or the transmission control unit 207.

The transmission control unit 207 inputs the set of date-and-time data and biological data to the transmitting unit 208.

The transmitting unit 208 receives the set of date-and-time data and measurement data from the transmission control unit 207, and transmits the received set of data to the data server 300 via the network. The transmitting unit 208 employs, for example, mobile communications or WLAN.

The data server 300 corresponds to a database that manages measurement data (mainly biological data) of a large number of users. In order to contribute to, for example, the user's health guidance, insurance subscription appraisal, health-promoting program score evaluation, etc., the data server 300 may transmit biological data of the user not only to the user himself or herself, but also to a health instructor, an insurance company, or a program operator, in response to an access from their PCs, etc.

<Others>

In the present embodiment, an example has been described in which each function of the data transmitting apparatus 100 and the data receiving apparatus 200 is implemented by a general-purpose CPU. However, part or all of the above functions may be implemented by one or more dedicated processors. Regarding the software configuration of each of the data transmitting apparatus 100 and the data receiving apparatus 200, functions may be suitably omitted, replaced, or added according to the embodiment.

§3 EXAMPLE OF OPERATION

<Data Transmitting Apparatus>

Figure 10:
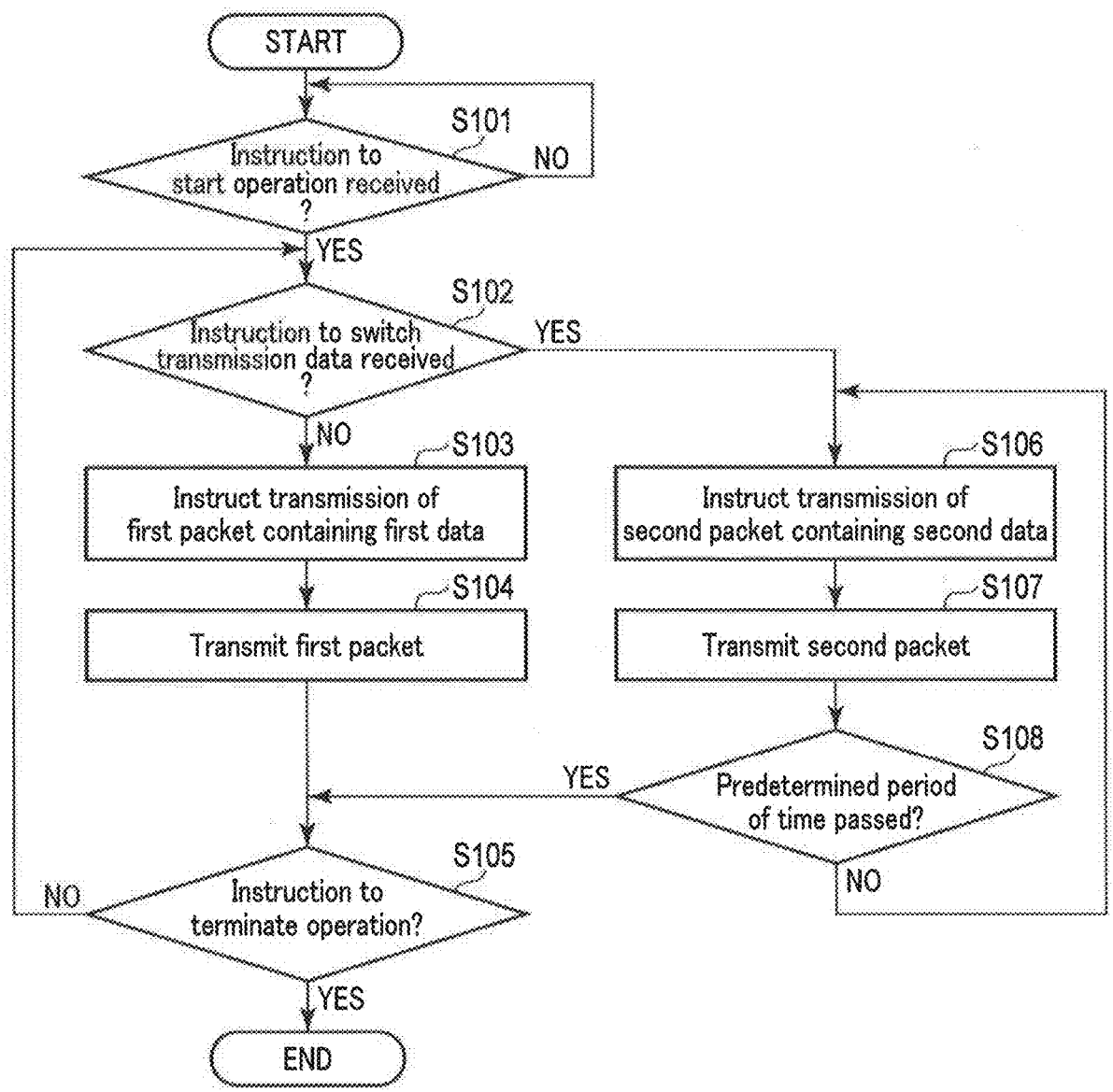
FIG. 10 is a flowchart showing an example of a data transmission process in the data transmitting apparatus according to the embodiment.

Next, an operation example of the data transmitting apparatus 100 will be described, with reference to FIG. 10. FIG. 10 is a flowchart showing an example of an operation of the data transmitting apparatus 100. It is to be noted that the processing procedure to be described below is merely an example, and each process may be varied where possible. In the processing procedure to be described below, the steps may be suitably omitted, substituted, and/or added, according to the embodiment.

As shown in FIG. 10, if the input unit 101 of the data transmitting apparatus 100 does not accept the second user input (step S102, NO) after accepting the first user input (step S101, YES), the transmission control unit 102 instructs transmission of the first packet containing the first data based on the first user input (step S103). For example, the transmission control unit 102 instructs, based on the first user input, commencement of transmission of the first packet, and also instructs continuation of the transmission of the first packet. The transmitting unit 103 continuously transmits a first packet for unidirectional communications based on an instruction to continuously transmit the first packet (step S104).

If the input unit 101 does not accept the first user input that instructs commencement of the operation (step S101, NO), neither the first packet nor the second packet is transmitted.

Alternatively, in response to the power-supply control unit 109 instructing, based on the first user input, commencement of supply of the power-supply voltage, the power-supply unit 110 may supply the power-supply voltage, and then the transmission control unit 102 may instruct transmission of the first packet containing the first data.

If the input unit 101 accepts neither the third user input that instructs termination of the operation (step S105, NO) nor the second user input (step S102, NO), the transmission control unit 102 continues instructing transmission of the first packet containing the first data (step S103). Thereby, the first packet containing the first data is repeatedly transmitted (step S104). When the first data is transmitted in N first packets via division of the first data to be transmitted into N items of divisional data (where N is an integer equal to or greater than 2), the transmission control unit 102 instructs repeated transmission of a single packet group consisting of N first packets.

If the input unit 101 accepts the first user input (step S101, YES), and then accepts the second user input (step S102, YES), the transmission control unit 102 instructs transmission of the second packet containing the second data, in place of transmission of the first packet containing the first data, based on the second user input (step S106). The transmitting unit 103 transmits, based on the instruction to transmit the second packet, a second packet through unidirectional communications (step S107).

If the predetermined period of time has not passed (step S108, NO), the transmission control unit 102 continues instructing transmission of the second packet containing the second data (step S106). Thereby, the second packet containing the second data is repeatedly transmitted (step S107). When the second data to be transmitted is divided into N items of divisional data (where N is an integer equal to or greater than 2) and the second data is transmitted in N second packets, the transmission control unit 102 instructs repeated transmission of a single packet group consisting of N second packets.

If the predetermined period of time has passed (step S108, YES) and the input unit 101 accepts neither the third user input that instructs the termination of the operation (step S105, NO) nor the second user input that instructs the switching of the transmission data (step S102, NO), the transmission control unit 102 instructs the transmission of the first packet containing the first data, in place of the instruction to transmit the second packet (step S103). Thus, subsequent to passage of the predetermined period of time, the processing returns to transmission of the first packet containing the first data.

<Data Receiving Apparatus>

Figure 11:
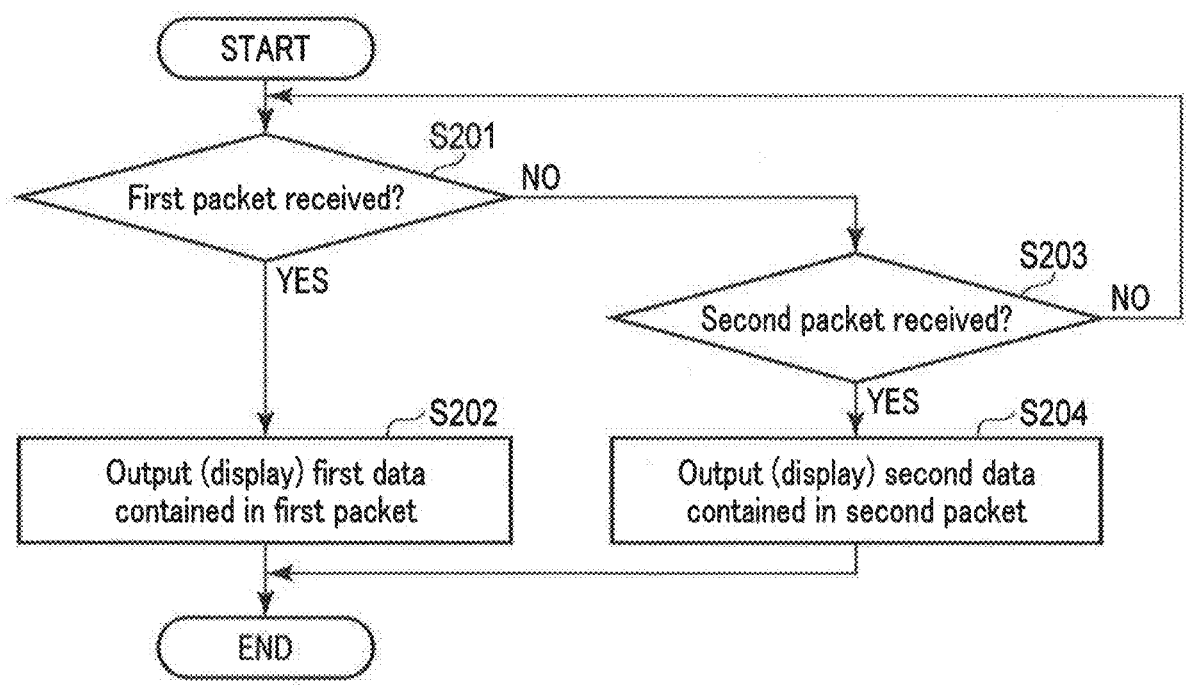
FIG. 11 is a flowchart showing an example of a data reception process in the data receiving apparatus according to the embodiment.

Next, an operation example of the data receiving apparatus 200 will be described, with reference to FIG. 11. FIG. 11 is a flowchart showing an example of the operation of the data receiving apparatus 200. It is to be noted that the processing procedure to be described below is merely an example, and each process may be varied where possible. In the processing procedure to be described below, the steps may be suitably omitted, substituted, and/or added, according to the embodiment.

The operation example of FIG. 11 is commenced when the receiving unit 201 of the data receiving apparatus 200 receives a radio signal that carries a BLE advertisement packet from the data transmitting apparatus 100 and obtains a reception signal.

When the receiving unit 201 receives the first packet (step S201, YES), the data processing unit 202 fetches a first packet from the reception signal, fetches first data from the first packet, and outputs the fetched first data (step S202). For example, the data processing unit 202 outputs the fetched first data to the display control unit 205, and the display control unit 205 generates first display data based on the first data, and inputs the generated first display data on the display unit 108. The display unit. 108 displays a first image based on the first display data input from the display control unit 107.

The first image includes, for example, transmission-related information related to transmission of biological data. The transmission-related information includes at least one of transmission history information on biological data and support information that guides the operation for transmitting the biological data. The transmission history information includes at least one of information on the presence or absence of yet-to-be-transmitted biological data, and information on the number of items of yet-to-be-transmitted biological data. The support information includes an operation procedure, etc. for causing the data transmitting apparatus 100 to transmit the second data.

When the receiving unit 201 does not receive the first packet. (step S201, NO) but receives the second packet (step S203, YES), the data processing unit 202 fetches a second packet from the reception signal, fetches second data from the second packet, and outputs the fetched second data (step S204). For example, the data processing unit 202 outputs the fetched second data to the display control unit 205, and the display control unit 205 generates second display data based on the second data, and inputs the generated second display data on the display unit 206. The display unit 206 displays a second image based on the second display data input from the display control unit 205.

For example, the second image includes biological data and date-and-time data associated with the biological data, and the biological data includes blood pressure data.

[Functions and Effects]

As described above, in the present embodiment, the data transmitting apparatus transmits, based on acceptance of the first user input, a first packet containing first data through unidirectional communications, and continues transmission of the first packet through unidirectional communications until the second or third user input is subseguently accepted. It is thereby possible to transmit first data, which is not confidential, to the data receiving apparatus capable of receiving a first packet, without the need for pairing or complicated communication procedures. The data receiving apparatus that has received the first packet in the communication area of the data transmitting apparatus is capable of displaying the first data. The first data includes, for example, transmission-related information related to transmission of biological data, and the transmission-related information includes at least one of transmission history information on biological data and support information that guides the operation for transmitting the biological data. The user of the data receiving apparatus can recognize the transmission history of the biological data from the displayed information, and can recognize, from the support information that guides the operation for transmitting the biological data, the necessity of the operation (second user input) for receiving the biological data.

Based on the acceptance of the second user input, the data transmitting apparatus temporarily switches from transmission of the first data to transmission of the second data, and transmits a second packet containing the second data through unidirectional communications. It is thereby possible to temporarily transmit second data, which is confidential, to the data receiving apparatus capable of receiving a second packet, without the need for pairing or complicated communication procedures. Moreover, since the second data, which is confidential, is temporarily transmitted, a high degree of confidentiality of the confidential second data can be ensured, as compared to the first data, which is not confidential. Since the user who owns the data receiving apparatus is conscious of receiving the second data in operating the data transmitting apparatus, the data receiving apparatus temporarily stays approximately still at a short distance from the data transmitting apparatus. This allows the data receiving apparatus to stably receive second data, thereby reducing or preventing the loss of the second data.

§4 MODIFICATION

The embodiment of the present invention has been described in detail above; however, in every respect, the present embodiment described above is merely an illustration of the present invention. As a matter of course, various alternations and modifications can be made, without departing from the spirit of the invention. That is, in implementing the present invention, a specific configuration may be suitably adopted according to the above embodiment. The data appearing in the above embodiment has been described with natural language; however, in actuality, it is represented by pseudo language, a command, a parameter, machine language, etc. that can be recognized by a computer.

The second data may be, for example, data with a high degree of at least one of the elements including priority, importance, and confidentiality, as compared to the first data. By using such data as the second data, it is possible to reduce the possibility of failure to receive such data.

The second data may be large-sized data, as compared to the first data. Large-sized data is likely to be transmitted in a plurality of packets via division into a plurality of items of data. By using such data as the second data, it is possible to reduce the possibility of failure to receive such large-sized data.

The second data may be encrypted and transmitted, instead of encrypting the first data. For example, the data transmitting apparatus 100 encrypts the second data using a predetermined encryption method, and transmits the encrypted second data. The data receiving apparatus 200 receives the encrypted second data, and decrypts the received second data using a decryption method corresponding to the predetermined encryption method. According to the receiving apparatus corresponding to the data receiving apparatus 200 of the data transmission and reception system of the present embodiment, it is possible to decrypt the received second data using a decoding method corresponding to the predetermined encryption method. Even if another receiving apparatus not corresponding to the data receiving apparatus 200 receives the encrypted second data through unidirectional communications compliant with a communication standard such as BLE, the received second data cannot he decrypted. By thus encrypting and transmitting the second data, the degree of confidentiality of the second data can be increased.

Switching may be temporarily made from the transmission of the first data to transmission of the second data, immediately subsequent to the measurement of the amount related to the blood pressure. For example, upon receiving the blood pressure data acquired by the data acquisition unit 104, the data management unit 105 instructs the transmission control unit 102 to temporarily switch from the transmission of the first data to transmission of the second data. Thereafter, the transmission control unit 102 temporarily switches from the transmission of the first data to the transmission of the second data, similarly to the case of accepting the second user input. Immediately subsequent to the measurement of the amount related to the blood pressure, a user who desires to receive the blood pressure data, and who own the data receiving apparatus 200, often temporarily stays approximately still in the proximity of the data transmitting apparatus 100, thus allowing the data receiving apparatus 200 owned by such a user to stably receive the blood pressure data, and reducing the possibility of failure to receive data.

§5 ADDITIONAL DESCRIPTIONS

Part or all of the above embodiments may be described as in the additional descriptions to be given below, as well as the claims; however, the embodiments are not limited thereto.

(Additional Description 1)
A data transmitting apparatus including:
a memory; and
a processor connected to the memory,
wherein the processor is configured to function as:
(a) an input unit that selectively accents a first user input and a second user input, the first user input instructing transmission of first data, the second user input temporarily switching from transmission of the first data to transmission of second data;
(b) a transmission control unit that instructs, based on the first user input, transmission of a first packet, and temporarily instructs, based on the second user input, transmission of a second packet in place of the instruction to transmit the first packet, the first packet containing the first data, the second packet containing the second data; and
(c) a transmitting unit that transmits the first packet through a unidirectional communication based on the instruction to transmit the first packet, and that transmits the second packet through a unidirectional communication based on the instruction to transmit the second packet.

REFERENCE SIGNS LIST

100: Data transmitting apparatus
101: Input unit
102: Transmission control unit
103: Transmitting unit
104: Data acquisition unit
105: Data management unit
106: Data storage unit
107: Display control unit
108: Display unit
109: Power supply control unit
110: Power-supply unit
111: Control unit
112: Storage unit
113: Communication interface
114: Input device
115: Output device
116: External interface
117: Battery
118: Biological sensor
200: Data receiving apparatus
201: Receiving unit
202: Data processing unit.
203: Data storing unit
204: Input unit
205: Display control unit
206: Display unit
207: Transmission control unit
208: Transmitting unit
211: Control unit
212: Storage unit
213: Communication interface
214: Input device
215: Output device
216: External interface
300: Data server

What is claimed is:

1. A data transmitting apparatus comprising:
an input unit that selectively accepts a first user input and a second user input, the first user input instructing transmission of first data which is non-confidential, the second user input temporarily switching from transmission of the first data to transmission of second data which is confidential;
a controller that instructs, based on the first user input, repeated transmission of a first packet, and instructs, based on the second user input, repeated transmission of a second packet over a predetermined period of time in place of the instruction to repeatedly transmit the first packet and then instructs repeated transmission of the first packet subsequent to passage of the predetermined period of time, the first packet containing the first data, the second packet containing the second data; and
a transmitter that repeatedly transmits the first packet through a unidirectional communication based on the instruction to repeatedly transmit the first packet, and that transmits the second packet over the predetermined period of time through a unidirectional communication and then repeatedly transmits the first packet subsequent to the passage of the predetermined period of time, based on the instruction to repeatedly transmit the second packet over the predetermined period of time and the instruction to repeatedly transmit the first packet subsequent to the passage of the predetermined period of time.

2. The data transmitting apparatus according to claim 1, wherein the first data includes transmission-related information related to transmission of biological data.

3. The data transmitting apparatus according to claim 2, wherein the transmission-related information includes transmission history information of the biological data.

4. The data transmitting apparatus according to claim 2, wherein the transmission-related information includes support information that guides an operation to transmit the biological data.

5. The data transmitting apparatus according to claim 2, wherein the second data includes the biological data.

* * * * *